United States Patent [19]

Zuckerman et al.

[11] Patent Number: 4,689,231

[45] Date of Patent: Aug. 25, 1987

[54] METHOD OF PROTECTING PLANTS FROM NEMATODES

[75] Inventors: Bert M. Zuckerman, Hadley, Mass.; Hans-Boerje Jansson, Lund, Sweden

[73] Assignee: Uniroyal Chemical Company, Inc., Middlebury, Conn.

[21] Appl. No.: 750,382

[22] Filed: Jun. 28, 1985

[51] Int. Cl.$^4$ ............................................. A61K 35/78
[52] U.S. Cl. .......................... 424/195.1; 424/DIG. 10
[58] Field of Search ............... 424/195.1, 93, DIG. 10

[56] References Cited

PUBLICATIONS

U. Durschner, "Mitteilungen aus der Biologischen Bundesanstalt" No. 217, Dec. 1983, pp. 1–83, Kommissionsverlag Paul Parey, Berlin DE.
Saikawa, Canadian J. of Botany 6(1980), 2019–2023.
Jansson et al., Antonie van Leeuwenhoek 50(1984), 321–327.
Giuma et al., Soil Biology & Chemistry 6(1974), 217–220.
Jansson, Trans. Br. Mycol. Soc. 79(1982) 25–29.
Jansson et al., J. of General Microbiology (1983) 129, 1121–1126.
Jansson, Microbial Ecology 8, (1982), 233–240.
Mandau, Phytopathology 52, 611–615 (1962).
Cooke, Phytopathology 58, 909–913 (1968).

*Primary Examiner*—Johnnie R. Brown
*Assistant Examiner*—John W. Rollins
*Attorney, Agent, or Firm*—William E. Dickheiser

[57] ABSTRACT

A method for protecting plants from nematodes comprising applying to the soil wherein nematodes may attack such plants a nematicidally effective amount of a composition comprised of *Meria coniospora* spores and a suitable nonliving carrier. Also, compositions comprising such spores and certain suitable carriers are disclosed.

11 Claims, No Drawings

METHOD OF PROTECTING PLANTS FROM NEMATODES

FIELD OF THE INVENTION

This invention is directed to a method for protecting plants from nematodes, which method involves applying to the soil wherein nematodes may attack such plants a nematicidally effective amount of a composition comprised of *Meria coniospora* spores and a suitable nonliving carrier. In another aspect, this invention is directed to compositions comprised of such spores and certain suitable nonliving carriers.

BACKGROUND OF THE INVENTION

The destruction by nematodes, especially so-called root-knot nematodes, of valuable field crops presents a serious problem to agriculture. Field crops in need of protection from nematodes include soybeans, corn, peanuts, cotton, alfalfa and tobacco. In addition, vegetables, such as tomatoes, potatoes, sugarbeet, carrots and the like, as well as fruits, nuts, ornamentals and seed bed crops such as apples, peaches, peas, citrus fruit and grapes may also require protection from the ravages of nematodes.

In the past, control of nematodes has generally required the application of chemical nematicides to fields. However, nematodes have exhibited a tendency to develop immunity to most chemical nematicides. Moreover, in many instances, such application of chemical nematicides to fields is environmentally undesirable.

Although it would be desirable to employ natural means, particularly nematophagous fungi, to control nematodes, in the past attempts to employ such fungi in non-sterile soil have proved to be ineffective. Nematophagous fungi are generally divided into two catagories, i.e., (1) nematode-trapping fungi which produce mechanical or adhesive traps: and (2) endoparasitic fungi which infect nematodes when their conidia (spores) are ingested or adhere to the cuticle of the worms.

R. Mankau, in "Soil Fungistasis and Nematophagus Fungi", Phytopathology, 52, 611–615 (1962) notes that "several unsuccessful attempts have been made in the past to introduce nematode-trapping fungi into soil and effect a biological control of plant-parasitic nematodes", although he states that one group of researchers have demonstrated "a moderate, but statistically significant, reduction of nematode injury to pineapple plants". R. Cooke, in "Relationships between Nematode-Destroying Fungi and Soil-Borne Phytonematodes", Phytopathology, 58 909–913 (1968), draws a similar conclusion about nematode-trapping fungi indicating that "the arbitrary addition of fungi or organic amendments to soil is likely to prove no more fruitful in the future than it has in the past".

Past experience with endoparasitic nematophagous fungi has generally indicated that the application of these species would similarly not control nematodes to any desirable degree. Thus, A. Y. Guima et al in "Potential of Nematoctonus Conida for Biological Control of Soil-Borne Phytonematodes", *Soil Biology and Chemistry*, 6, 217–220 (1974), indicate that although some nematode control was achieved in sterilized soil, "natural nematode populations in non-sterile soil were not affected by the introduction of Nematoctonus (i.e., *N. concurrens* and *N. haptocladus*—both of which are endoparasitic fungi) conidia even at the highest spore concentrations (i.e., $1.25 \times 10^5$ spores per gram of moist soil)".

Thus, it is completely unexpected that the application of a composition comprised of (a) *Meria coniospora* fungus spores and (b) a suitable nonliving carrier to the soil will significantly reduce nematode infestation, even when said spores are present in ratios as small as 2 spores per nematode egg are added. This degree of control is even more unexpected in view of the disclosure in "Attraction of Nematodes to Endoparasitic Nematophagous Fungi", H. Jansson, *Trans. Br. mycol. Soc.*, 79 (1) 25–29 (1982) that although nematodes are attracted to conidia of *M. coniospora* a concentration of $0.5 \times 10^6$ spores per microliter was necessary to attract nematodes.

DESCRIPTION OF THE INVENTION

In one aspect, this invention is directed to a method for protecting plants from nematodes, which method comprises administering to the soil wherein nematodes may attack such plants a nematicidally effective amount of a composition comprising:
(a) *Meria coniospora* spores: and
(b) a suitable nonliving carrier.

another aspect, this invention is directed to a composition comprising:
(a) *Meria coniospora* spores; and
(b) at least one suitable nonliving carrier selected from the group consisting of (1) solid materials: (2) liquid materials comprising a non-aqueous liquid: and (3) aqueous dispersions comprising water and a dispersant.

The method of this invention involves that application of a composition comprising *Meria coniospora* spores and a nonliving carrier to that portion of the soil wherein nematodes may attack the plants to be protected. Such application may be accomplished by broadcasting, tilling in such composition, placing the composition in seed furrows, as well as by other similar means. Alternatively, the composition may be employed to plant roots or seeds prior to planting.

The composition employed in the process of this invention comprises *Meria coniospora* spores and a suitable nonliving carrier. The spores may be produced in sufficient numbers by any conventional fungal-culturing method which is well known to those skilled in the art. However, a particularly preferred method of culturing such spores involves inoculating *Meria coniospora* onto a liquid shake culture with a malt extract substrate, allowing such culture to grow to maturity, and then collecting the spores by flooding the culture dish with sterile water.

Carriers which may be employed in the process of this invention include solids, suitable non-aqueous liquids, and aqueous-based liquids.

Suitable solid carriers which may be employed in this invention include sand, vermiculite, activated carbon, ground corncobs, silicates such as talc, mica, attapulgite or pyrophyllite, and the like. The spores may be absorbed to the surface of such carriers by means well known to those skilled in the formulation art, prior to application to nematode infested loci.

One particularly preferred nonliving solid carrier comprises dried nematodes which had been infected with spores of *Meria coniospora*. In this embodiment, nematodes infected with spores of *Meria coniospora* are dried, preferably freeze-dried, causing the nematodes to die but not the spores. Such dried infected nematodes may be applied to nematode infested areas either as is or by absorbing such nematodes to a solid inert carrier prior to use. The moisture in the soil will revive the spores, which will then feed on the infected dead nematodes causing fungus to grow and producing still further spores which will be ready to infect any live parasitic nematodes present.

Any suitable non-aqueous liquid may also be employed as a carrier in this invention. Such liquids are suitable if they are nontoxic to both the spores and the plants to be protected, and if they may be readily dispersed into the soil. Often, such non-aqueous liquid will be mixed with a major or minor amount of water.

Another means for carrying out this invention is by preparing an aqueous dispersion of the spores or of the spores adsorbed on an inert carrier. Although water alone may be employed as a carrier in the process of this invention, it is preferred that a suitable dispersant be employed for stabilization. Suitable dispersants are disclosed in McCutcheon's *Detergents and Emulsifiers*, Allured Publishing Corporation (1970). These agents may be anionic, cationic or non-ionic. As is employed herein, the term "dispersant" includes surfactants.

The compositions used in the present invention may further comprise baits or other attractants which will attract nematodes. These substances are well known to those skilled in the nematocide art, and include certain chlorine or sodium-containing materials (such as $CaCl_2$ and the like), phermones and adenosine monophosphate.

The *Meria coniospora* spore-containing composition may be administered either alone or in combination with other pesticides such as insecticides, herbicides or bactericides, or with growth regulators, plant nutrients and the like. Care should be taken that none of the added ingredients are detrimental to the effectiveness of the nematicidal fungus.

Although the *Meria coniospora* spores are relatively hardy, it is preferred that such spores—either prior to being compounded with a carrier or after such compounding—be stored at relatively low temperatures, e. g. of about 5° to about 15° C.

It is advisable to determine the nematode concentration in the soil before the spores of the nematicidal fungus of this invention is applied.

Generally, the ratio of the number of spores of *Meria coniospora* to the number of nematodes and/or nematode eggs in the soil, should initially be about 2:1 or more, is preferably initially between about 10:1 and about 2000:1, and is most preferably initially between about 20:1 and about 200:1.

The process of this invention is effective against a wide range of nematodes, including *Meloidogyne spp.* such as *M. incognita* and *M. javanica; Anguina spp.* such as *A. tritici; Ditylenchus spp.* such as *D. destructor: Aphelenchus spp.* such as *A. avenae; Pratylenchus spp.* such as *P. penetrans: Aphelenchoides spp. such as A. fragariae; Heterodera spp.: Rotylenchulus spp.: Hirschmanniella spp.;* and *Globodera spp.*

EXAMPLES

The following Examples are intended to further illustrate the invention and are not intended to limit the scope of the invention in any manner whatsoever.

EXAMPLES 1-4 AND COMPARATIVE EXPERIMENT A

*Meria coniospora* Dreschler was cultured on diluted cornmeal agar (CMA 1:10, 1.5% agar) in petri plates. Conidia (spores) were collected by flooding the plates with sterile water. In Examples 1–4, a 1.0 ml aqueous suspension of conidia (in the concentrations indicated in Table 1 below) was added into a pot containing a twenty-day-old seedling tomato (*Lycopersicon esculentum* Mill. cv. Tiny Tim) in 250 cubic centimeters of steam sterilized commercial potting soil. After 24 hours, a suspension of 5,000 *Meloidogyne javanica* eggs in 1.0 ml of water was added to each of four depressions (each measuring 0.5×2.5 cm) in the soil of each pot. Each Example was replicated 10 times. In Comparative Experiment A, which was also replicated 10 times, no spores were added.

The inoculated pots were placed in a greenhouse kept at 30°–35° C. for 60 days after which time the number of root galls recorded.

The average results of such testing (rounded off to the nearest significant integer) are indicated in Table I.

TABLE I

| | Example or Comparative Experiment | | | | |
|---|---|---|---|---|---|
| | A | 1 | 2 | 3 | 4 |
| Spore Concentration Added | 0 | $1 \times 10^4$ | $1 \times 10^5$ | $1 \times 10^6$ | $1 \times 10^7$ |
| Spore to Egg Ratio[1] | 0 | 2 | 20 | 200 | 2000 |
| Number of Root Galls[2] | 25 | 15 | 5 | 1 | 1 |
| Damage Reduction %[3] | — | 40 | 80 | 96 | 96 |

[1]*Meria coniospora* spores per *M. javanica* egg.
[2]Numbers of root galls per plant.
[3]Calculated:
(No. of root galls, control − No. of root galls, experiment) × 100/(No. root galls, control).

The above data clearly indicate the surprisingly high reduction of damage to plant roots by the nematodes even at relatively low spore/nematode egg ratio.

EXAMPLES 5 AND 6 AND COMPARATIVE EXPERIMENTS B AND C

In each of Example 5 and Comparative Experiment B, ten pots each containing a twenty-day-old tomato seedling in 250 cubic centimeters sterilized soil were provided as described in Examples 1–4. In Example 6 and Comparative Experiment C, an identical number of tomato seedlings were provided, except that non-sterilized soil was present. To each pot of Examples 5 and 6 was added a water suspension containing $3.8\times10^6$ conidia of *Meria coniospora*. After a twenty-four hour period, a suspension containing 20,000 *Meloidogyne incognita* eggs was added to each pot. The pots were stored for 60 days in a greenhouse at 30°–35° C. The plants were then inspected for root galls. The average results of such testing are indicated in Table II.

TABLE II

| | Example or Comp. Example | | | |
|---|---|---|---|---|
| | B | C | 5 | 6 |
| Soil | Sterile | Non-sterile | Sterile | Non-sterile |
| Spore:Egg Ratio* | 0 | 0 | 190:1 | 190:1 |
| Galls Per Plant | 9.5 ± 1** | 11.0 ± 0.8 | 1.5 ± 0.4 | 3.1 ± 0.3 |
| Damage | — | — | 84.2*** | 71.8*** |

TABLE II-continued

| | Example or Comp. Example | | | |
|---|---|---|---|---|
| | B | C | 5 | 6 |
| Reduction % | | | | |

*Meria coniospora* spores per *M. incognita* egg.
**Data given as the mean ± standard error.
***Damage reduction based upon Comparative Experiment employing identical soil.

The above results indicate that the process of this invention provides substantial protection against nematodes even in non-sterile soil.

What is claimed is:

1. A method for protecting plants from nematodes comprising administering to the non-sterile soil wherein nematodes may attack such plants a nematocidally effective amount of a composition comprising:
   (a) *Meria coniospora* spores; and
   (b) a suitable nonliving carrier.

2. The method of claim 1 wherein said composition comprises dried spore-infected nematodes.

3. The method of claim 2 wherein said nematodes are freeze-dried.

4. The method of claim 1 wherein said composition comprises an aqueous suspension.

5. The method of claim 1 wherein said composition further comprises an attractant.

6. The method of claim 1 wherein said composition is employed in an amount such that about 2:1 or more spores per nematode and nematode egg is initially present in the treated soil.

7. The method of claim 6 wherein said composition is employed such that the ratio of spores to nematodes and nematode eggs in the treated area is initially between about 10:1 and about 2000:1.

8. The method of claim 7 wherein said composition is employed such that the ratio of spores to nematodes and nematode eggs in the treated area is initially between about 20:1 and about 200:1.

9. A composition comprising:
   (a) *Meria coniospora* spores; and
   (b) at least one suitable nonliving carrier selected from the group consisting of (1) solid materials; (2) liquid materials comprising a nonaqueous liquid; and (3) aqueous dispersions containing water and a dispersant.

10. The composition of claim 9 wherein said composition comprises freeze-dried spore-infected nematodes.

11. The composition of claim 9 wherein said composition further comprises an attractant.

* * * * *